(12) United States Patent
Ito et al.

(10) Patent No.: US 6,468,235 B2
(45) Date of Patent: Oct. 22, 2002

(54) FACIAL AESTHETIC TREATMENT APPARATUS

(75) Inventors: Kengo Ito; Kazuyasu Ikadai, both of Hikone (JP)

(73) Assignee: Matsushita Electric Works, Ltd., Osaka (JP)

(*) Notice: Subject to any disclaimer, the term of this patent is extended or adjusted under 35 U.S.C. 154(b) by 0 days.

(21) Appl. No.: 09/907,765

(22) Filed: Jul. 19, 2001

(65) Prior Publication Data

US 2001/0041848 A1 Nov. 15, 2001

Related U.S. Application Data

(62) Division of application No. 09/422,929, filed on Oct. 22, 1999.

(30) Foreign Application Priority Data

Oct. 26, 1998 (JP) .............................................. 10-304020

(51) Int. Cl.[7] .................................................. A61H 7/00
(52) U.S. Cl. ................................. 601/6; 601/7; 601/10; 601/12; 132/320
(58) Field of Search ........................... 601/6, 7, 10, 12, 601/159–161; 132/320, 218, 317

(56) References Cited

U.S. PATENT DOCUMENTS

| 3,763,854 | A | * | 10/1973 | Welch ........................ 15/415.1 |
| 3,906,940 | A | | 9/1975 | Kawada |
| 4,748,973 | A | | 6/1988 | Cho |
| 5,003,966 | A | | 4/1991 | Saka et al. ..................... 601/13 |
| 5,099,830 | A | | 3/1992 | Kishimoto ................... 601/161 |
| 5,377,701 | A | | 1/1995 | Fang |
| 5,891,064 | A | | 4/1999 | Van Herk et al. ............ 601/126 |
| 6,017,320 | A | * | 1/2000 | Bleeker et al. .............. 601/122 |
| 6,309,364 | B1 | * | 10/2001 | Cathaud et al. .............. 601/122 |

FOREIGN PATENT DOCUMENTS

| DE | 400 305 B | 12/1995 |
| GB | 2280 109 A | 1/1995 |
| JP | 53149443 | 12/1978 |
| JP | 5-37234 | 5/1993 |

* cited by examiner

Primary Examiner—Danton D. DeMille
Assistant Examiner—Quang D. Thanh
(74) Attorney, Agent, or Firm—Rader, Fishman & Grauer PLLC

(57) ABSTRACT

A facial aesthetic treatment apparatus includes a housing provided with a nozzle and a suction pump for developing a suction force. An attachment is mounted to the nozzle for applying the suction force to a facial skin for removal of sebum, dirt or the like debris from the facial skin. The apparatus is capable of regulating the suction force being applied to the skin, and particularly minimizing the suction force immediately in response to the user's action of ceasing the treatment, thereby making it easy to remove the attachment from the facial skin and therefore reducing a risk of causing a pain and leaving the purpuric mark as well. A regulator is incorporated to regulate the suction force being applied to the facial skin for easy and safe removal of the suction force.

2 Claims, 17 Drawing Sheets

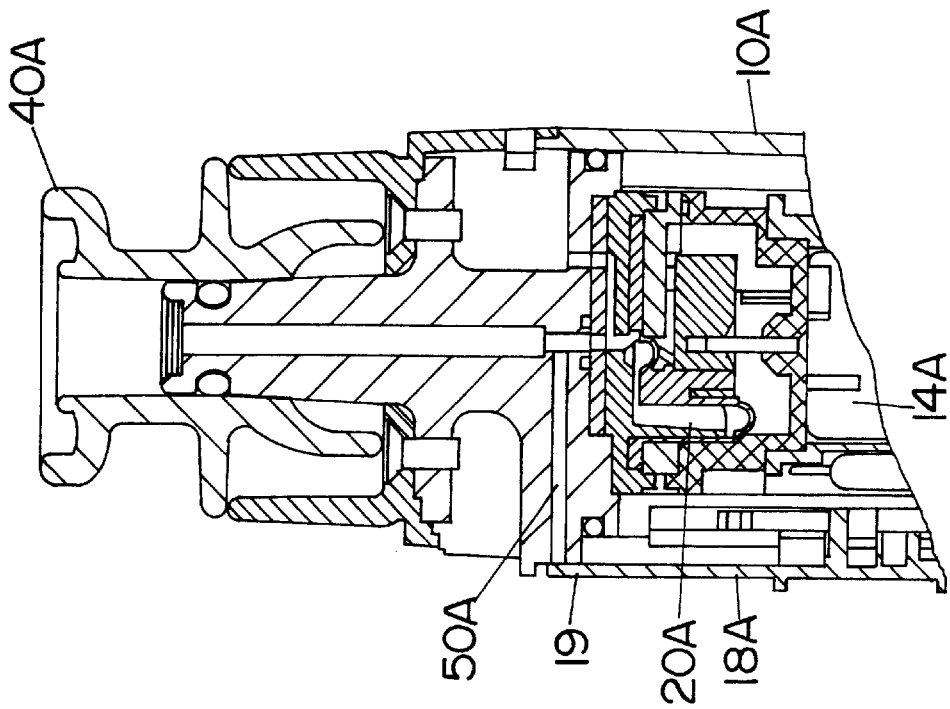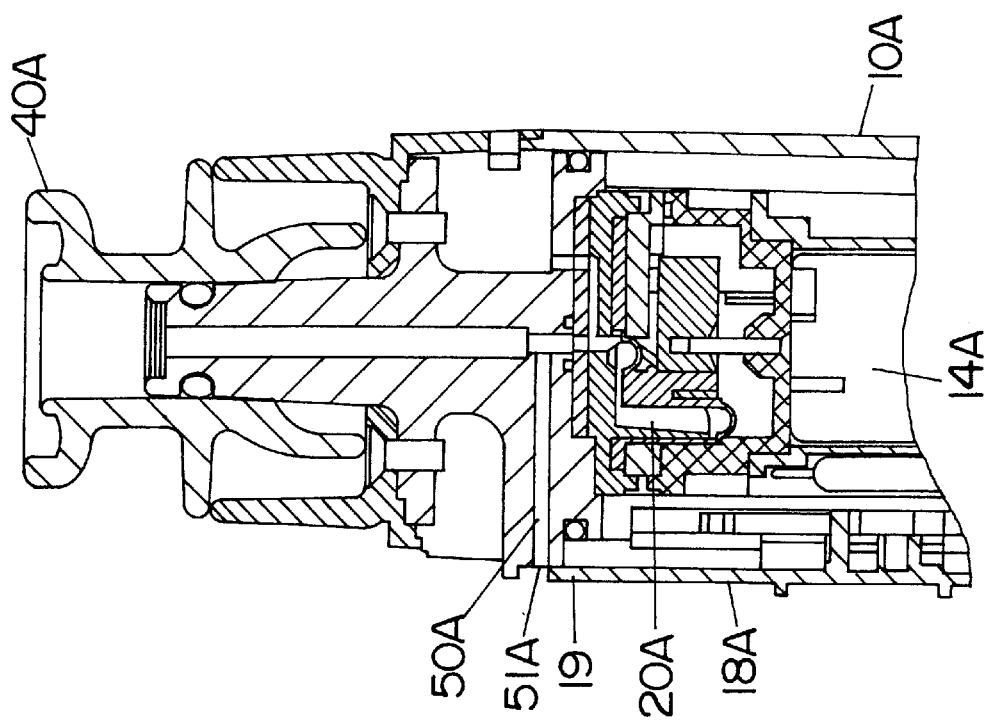

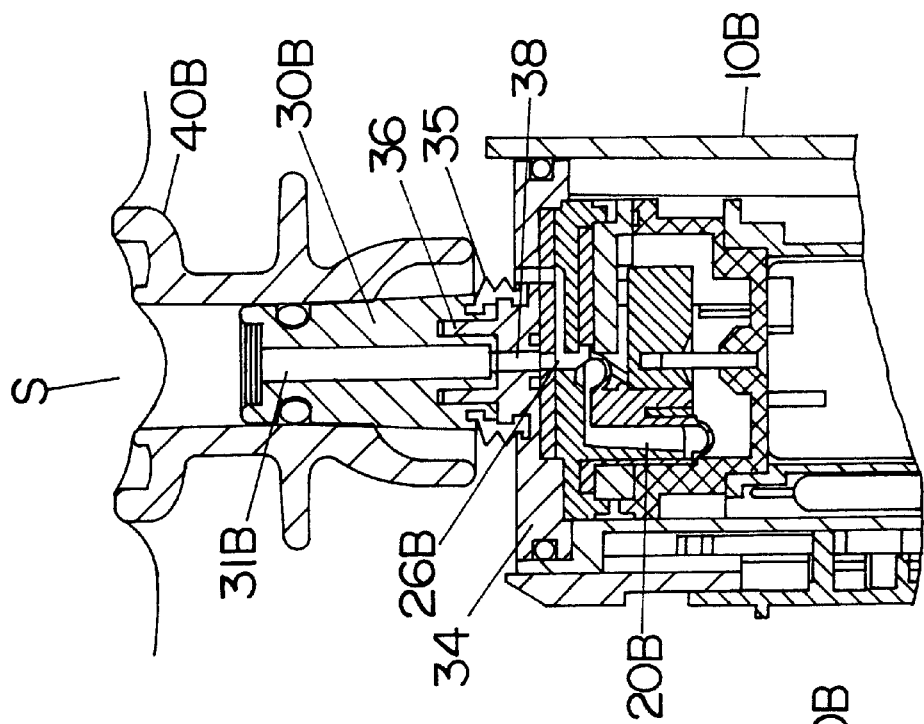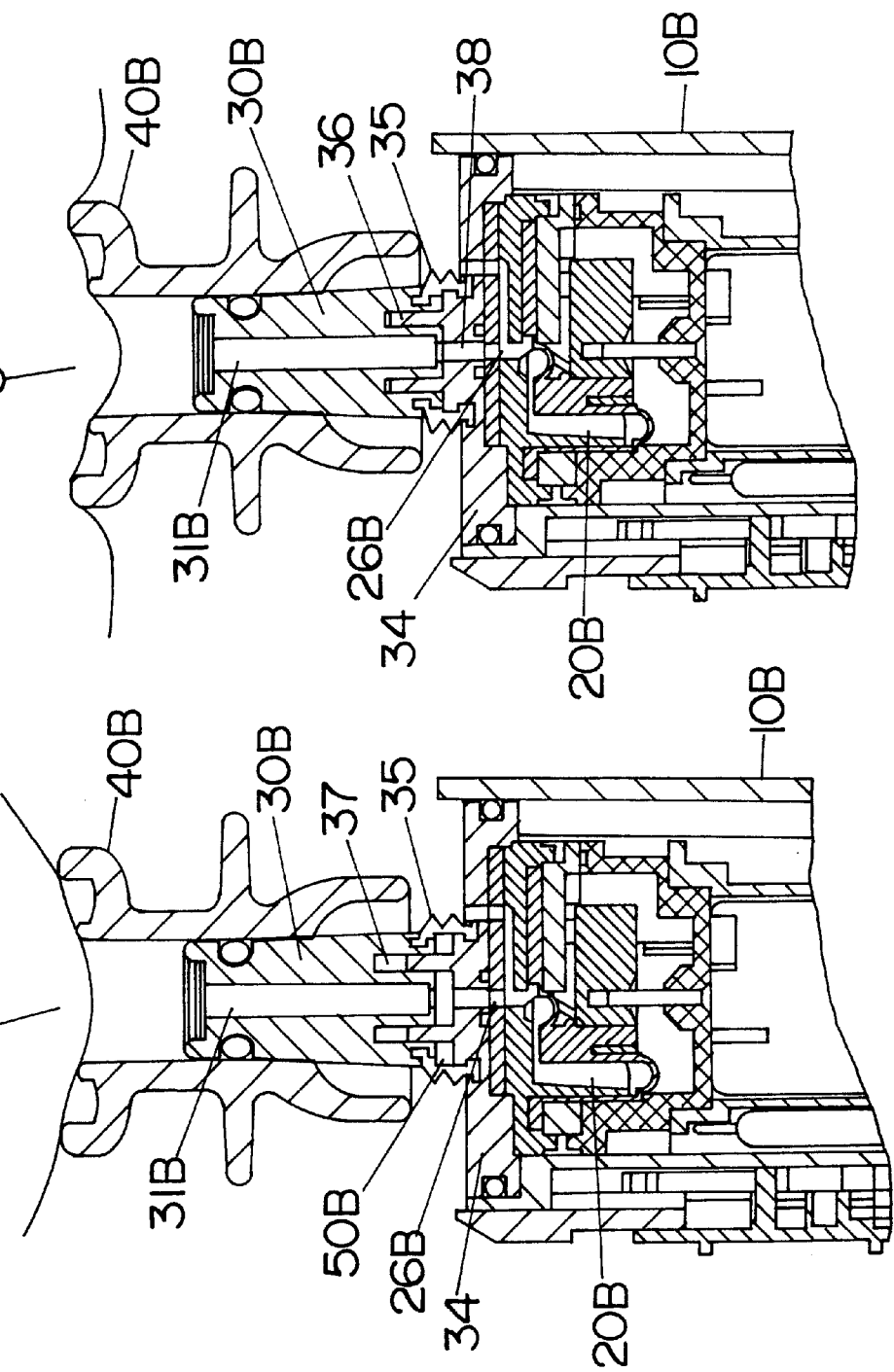

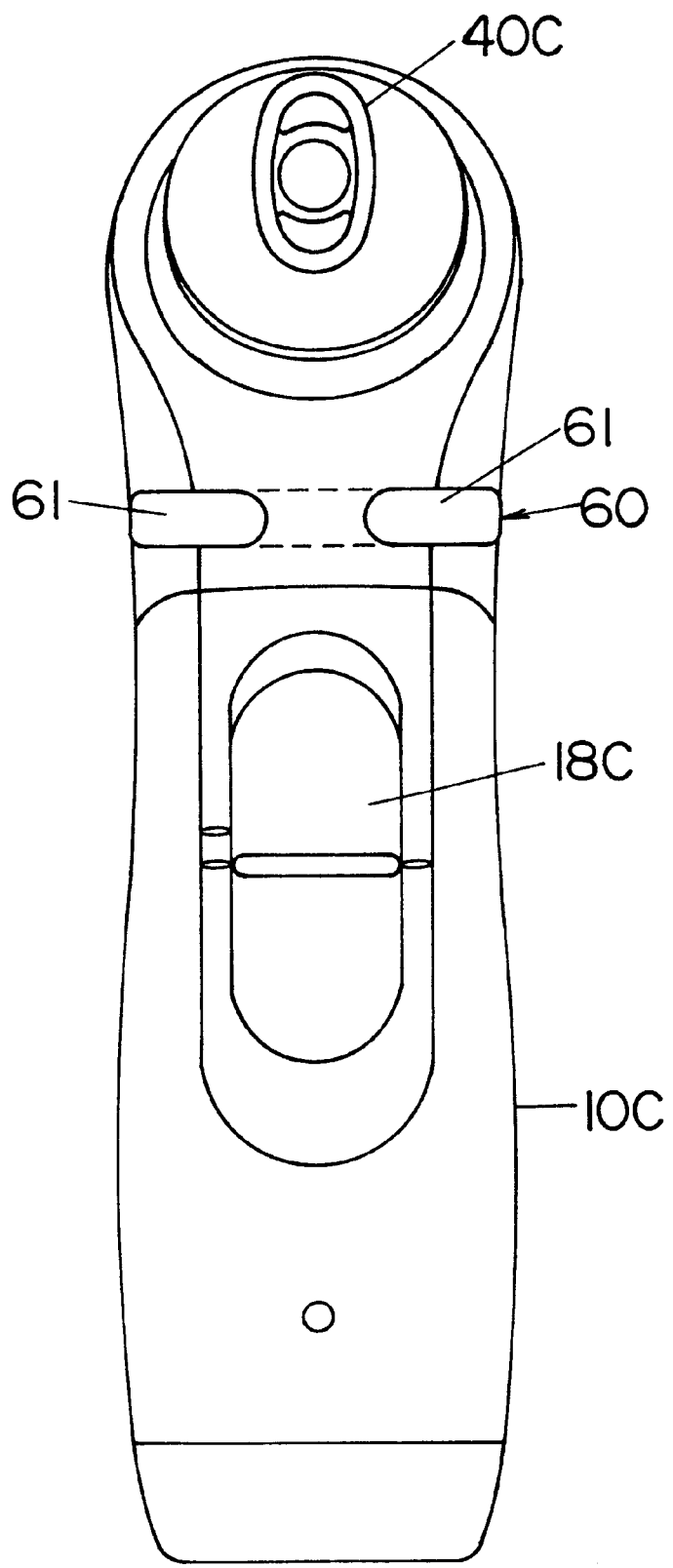

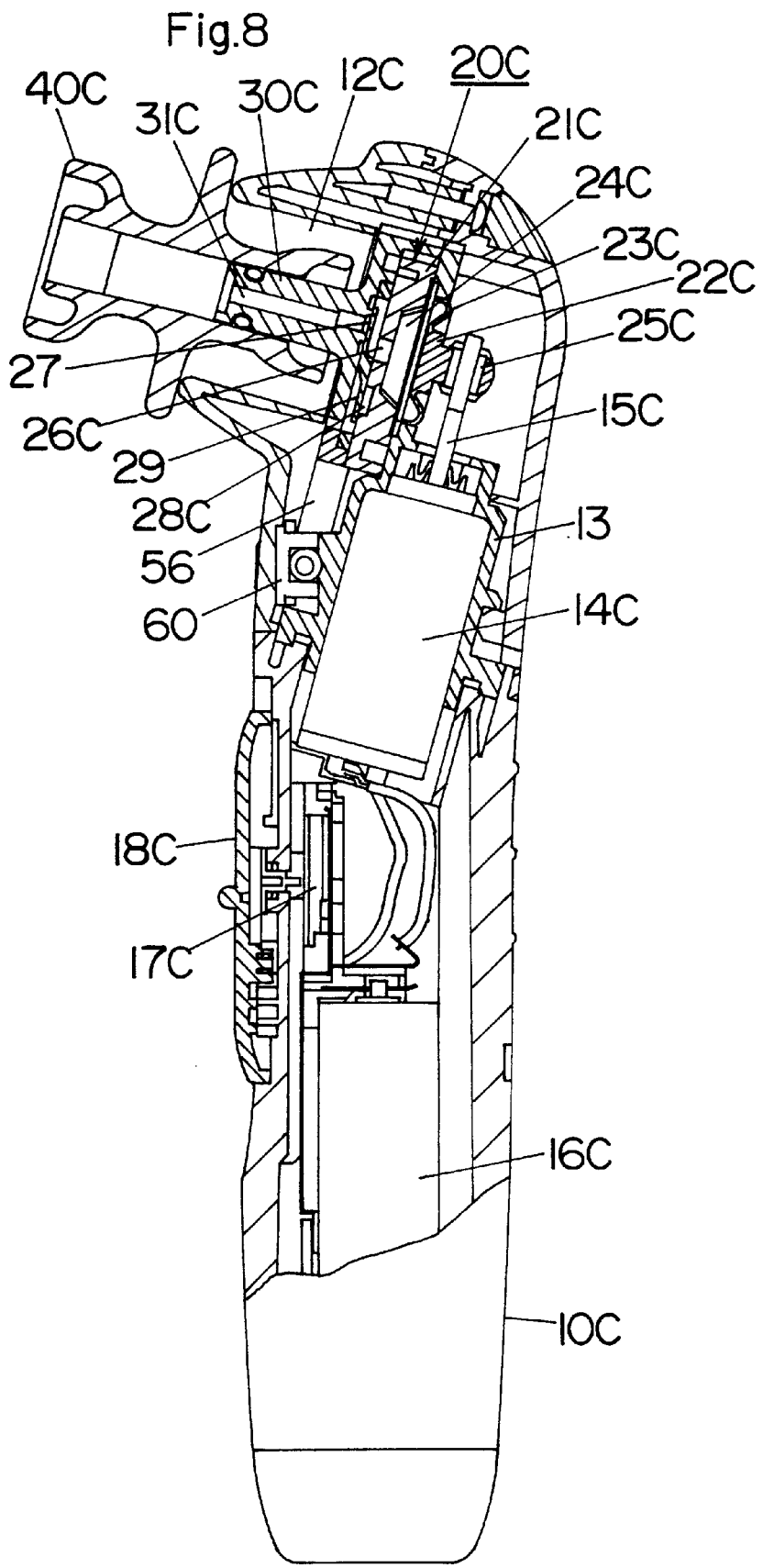

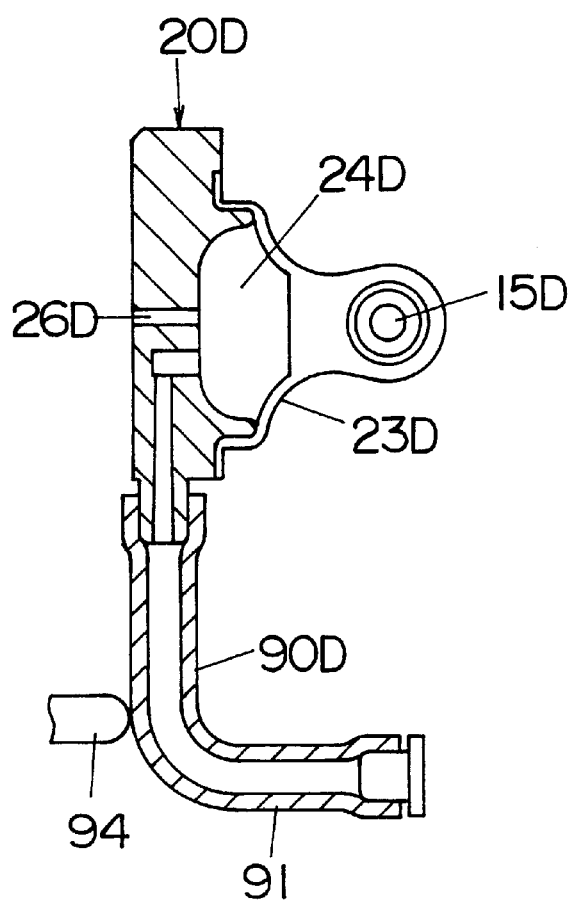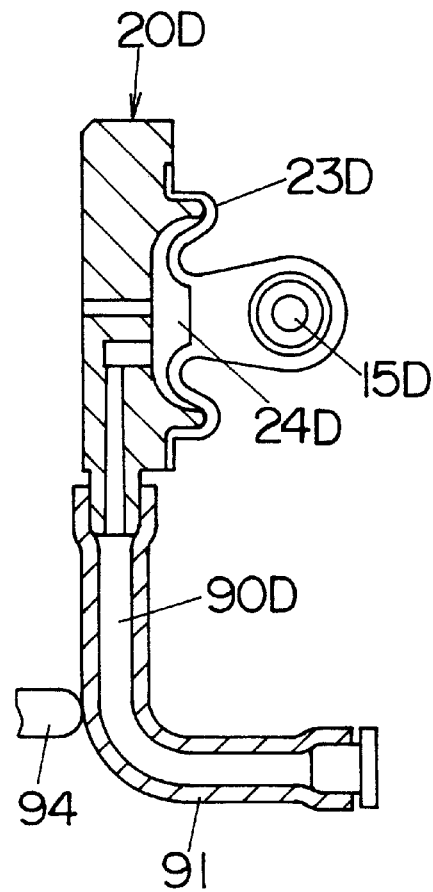

FACIAL AESTHETIC TREATMENT APPARATUS

This is a Division of application Ser. No. 09/422,929 filed Oct. 22, 1999. The disclosure of the prior application is hereby incorporated by reference herein in its entirety.

BACKGROUND OF THE INVENTION

1. Field of the Invention

The present invention is directed to a facial aesthetic treatment apparatus for removing sebum, dirt or the like debris from a facial skin by application of air suction to the skin, and more particularly to such apparatus with a capability of adjusting the suction force.

2. Description of the Prior Art

As disclosed in Japanese Utility Model Publication No. 5-37234, a prior facial aesthetic treatment apparatus is known to include a housing incorporating a suction pump for developing a suction force and an attachment adapted in use to be placed in contact with a facial skin for applying the suction force in order to remove the sebum or the like debris. When applying the suction force over a prolonged time to a delicate portion of the skin, there remains a possibility of bringing about undesired pain or even bruise, i.e., purpuric mark in the skin portion as a result of that the sucked portion of the skin is forced to bulge to such an extent of breaking capillary vessels in that portion.

SUMMARY OF THE INVENTION

The above problem has been reduced by the present invention. Therefore, it is a primary object of the present invention to provide an improved facial aesthetic treatment apparatus which is capable of regulating the suction force being applied to the skin, and particularly minimizing the suction force immediately as soon as the user intends to stop operating the apparatus, thereby making it easy to remove the attachment from the facial skin and therefore reducing a risk of causing a pain and leaving the purpuric mark as well.

The apparatus in accordance with the present invention includes a housing provided with a nozzle and a suction pump for developing a suction force through the nozzle. A tubular attachment is adapted to be coupled to the nozzle for applying the suction force to a facial skin for removing sebum, dirt or the like debris from the facial skin. The characterizing feature of the present invention resides in that the apparatus includes a regulator which alters pump characteristics, for example, load or capacity of the suction pump to regulate the suction force being applied through the nozzle to the facial skin in order to achieve the above-mentioned object.

In one preferred embodiment, the regulator comprises a bypass suction path extending from the suction pump to an open-air end which is accessible by a finger of a user's hand grasping the housing so as to selectively close and open said open-air end. Thus, the bypass suction path can be immediately opened simply by releasing a finger, i.e., a thumb of the user's hand gripping the housing from the open-air end. Therefore, the user can be easy to minimize the suction force, thereby facilitating to stop applying the suction force in a prompt response to the user's intention. Further, since the open-air end can be closed as well simply by placing the thumb closely on the open-air end, it is easy and convenient to apply the suction force intermittently while moving the attachment across a wide area of the facial skin, giving rise to an improved handling of the apparatus.

A flexible cover may be provided on the exterior of the housing to be accessible by the finger of the user for closing the opening the open-air end. With the use of the cover, the open-air end can be free from foreign matter which might otherwise clog the open-air end.

A switch handle provided on the exterior of the housing may be interlocked with a shutter which closes and opens the open-air end respectively when the switch handle comes into -an ON position of operating the suction pump and into an OFF position of ceasing the suction pump. Thus, the suction force can be released through the open-air end from the facial skin immediately upon turning off the switch handle, assuring a safe removal of the attachment from the skin. Otherwise the suction force would continue being applied to the skin even after turning off the switch handle, thereby making it difficult to remove the attachment from the skin.

Further, the regulator may comprise a contractible bypass suction path extending from the suction pump to an open end, and a mechanism of floatingly supporting the nozzle to the housing for allowing the nozzle to move between an extended position of causing the attachment to be disengaged from the facial skin and a retracted position of causing the attachment to be held in pressed contact with the facial skin. The nozzle is forced into the retracted position as a consequence of pressing the attachment against the skin, thereby closing the bypass suction path for applying the suction force to the skin. When the user moves the housing away from the skin, the nozzle is forced into the extended position as the attachment still stick to the skin due to the sucking force. Immediately upon the nozzle moving into the extended position, the bypass suction path is opened to release the suction force, thereby allowing the attachment to be readily disengaged from the skin for safe and rapid removal of the attachment from the skin.

In another embodiment, the regulator comprises a resilient tube extending from the nozzle to an open-air end to define the bypass suction path, and an actuator held in contactable relation with a portion of the resilient tube for pressing it to close the bypass suction path to a varying extent. Thus, the suction force being applied to the skin can be adjusted from maximum to minimum for an optimum facial treatment as well as for safe removal of the attachment from the skin.

In this connection, the actuator is mounted to the housing which is of an elongated configuration having a longitudinal axis. The actuator includes a pair of button sections exposed on an exterior of the housing to be accessibly by a finger of the user's hand gripping the housing. The pair of the button sections are arranged on opposite sides of the housing about the longitudinal axis such that both of a left-handed and right-handed user can be easy to manipulate the actuator in an convenient manner for adjusting the suction force.

In a further embodiment, the suction pump is configured to include a main pump responsible for developing the suction force and an auxiliary chamber communicating with the main pump chamber. The regulator is realized by an actuator which varies a volume of the auxiliary chamber in order to variably adjust the suction force being applied to the skin for an optimum facial treatment. The auxiliary chamber may be formed by a resilient tube extending from the main pump chamber and terminating at a closed end. The actuator is in a contactable relation with a portion of the resilient tube for pressing it to vary the volume of the auxiliary chamber.

In a still further embodiment, the apparatus includes a humidifier which is disposed in an adjacent relation to the nozzle to direct a stream of mist towards the facial skin for enhancing the facial treatment. The humidifier makes the use of an exhaust air from suction pump. For this purpose, an exhaust path is provided to extend from an exhaust port of the pump to an exit port which opens to an outside air. The humidifier comprises a spray nozzle with a constriction, a water tank supplying the water to the constriction, a switch for selectively opening and closing the exit port, and a bypass exhaust path diverging from the exhaust path at a portion between the exhaust port and the exit port to the spray nozzle. When the switch closes the exit port, the bypass exhaust path is made active to introduce a pressurized air into the spray nozzle for giving an air jet flowing through the constriction. Thus, the water at the constriction is sucked up into the air jet for generating the stream of mist. Accordingly, it is a further object of the present invention to provide a facial treatment apparatus which is capable of enhancing the removal of sebum, dirt or the like debris with an aid of the mist, while making the use of the suction pump for generation of the mist.

These and still other objects and advantageous features of the present invention will become more apparent from the following description of the embodiments when taken in conjunction with the attached drawings.

BRIEF DESCRIPTION OF THE DRAWINGS

FIGS. 5A and 5B are vertical sections of a major portion of a facial aesthetic treatment apparatus in accordance with a second embodiment of the present invention, respectively illustrating OFF and ON conditions;

FIGS. 6A and 6B are vertical sections of a major portion of a facial aesthetic treatment apparatus in accordance with a third embodiment of the present invention, respectively illustrating different operating conditions;

FIG. 7 is a front view of a facial aesthetic treatment apparatus in accordance a fourth embodiment of the present invention;

FIG. 8 is a vertical section of the above apparatus;

FIGS. 19A and 19B are diagrams illustrating a pumping operation of the above apparatus.

DETAILED DESCRIPTION OF THE EMBODIMENT

Figure 1:
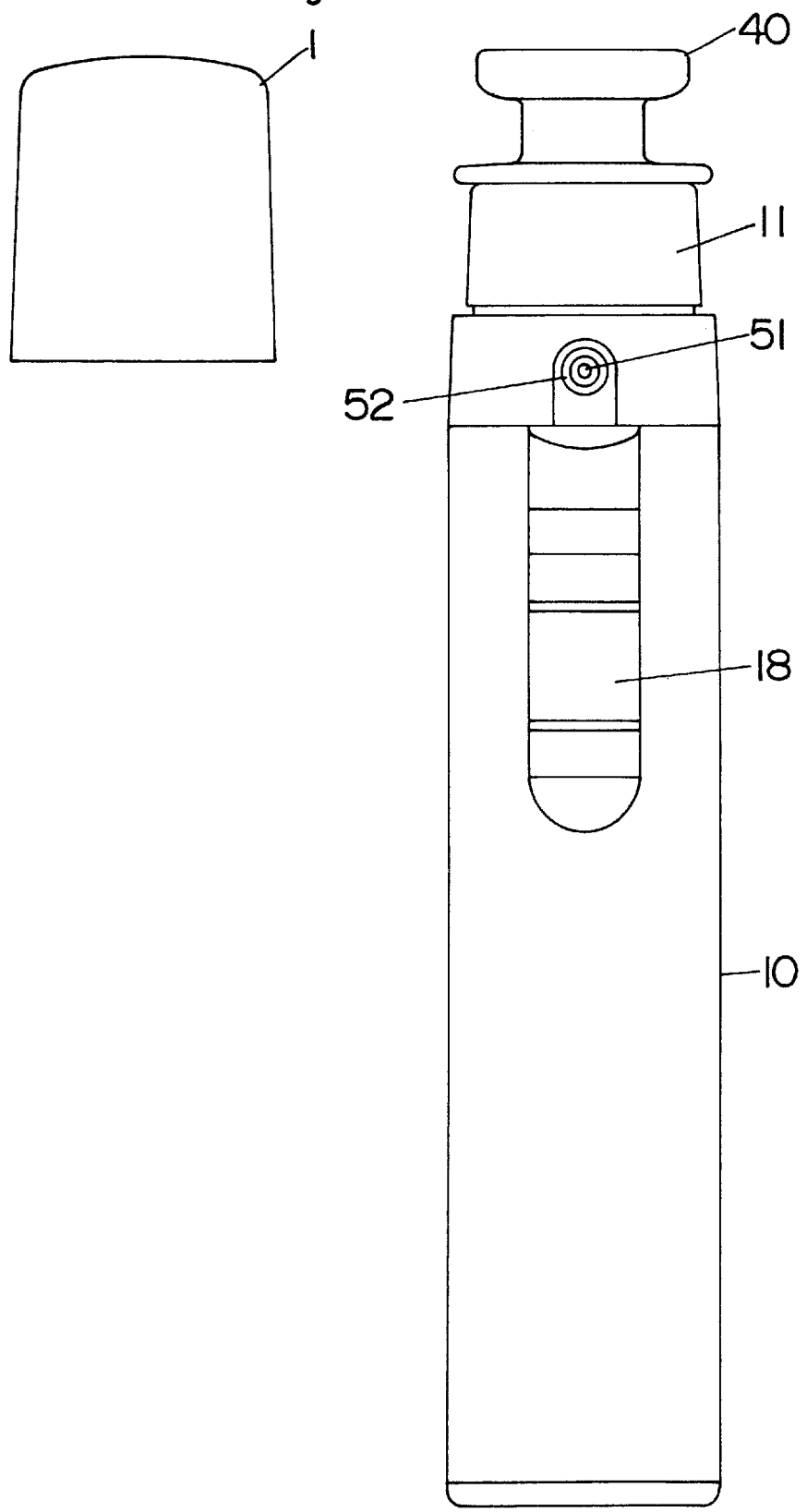
FIG. 1 is a front view of a facial aesthetic treatment apparatus in accordance with a first embodiment of the present invention.
Figure 2:
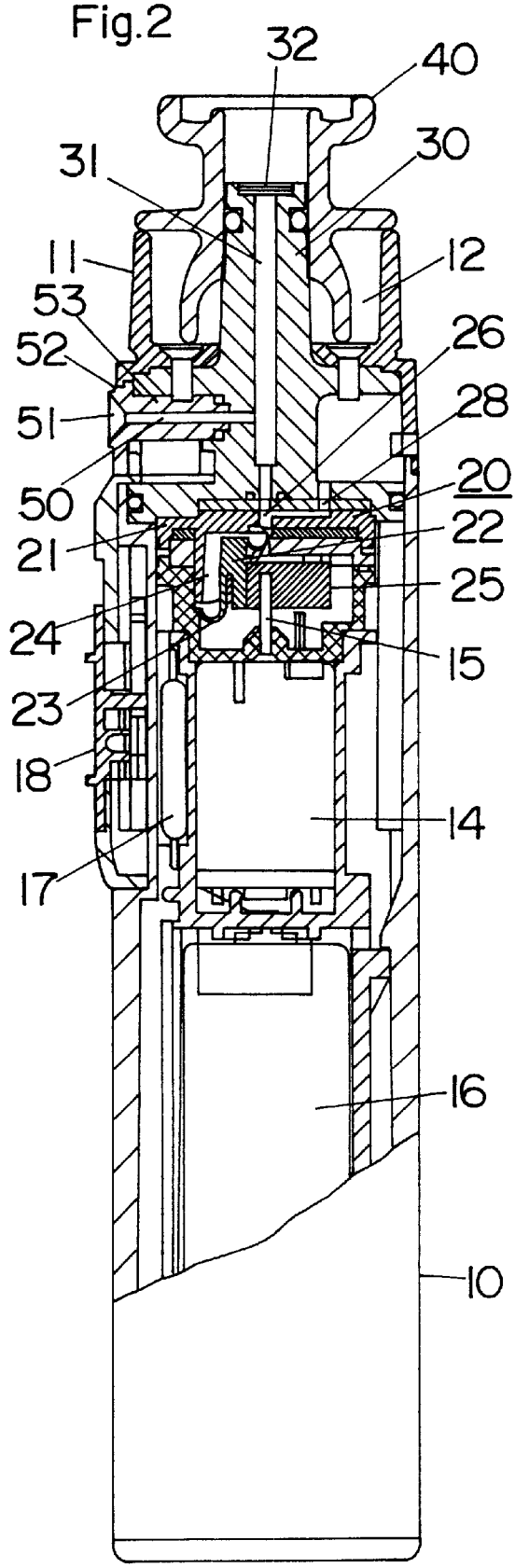
FIG. 2 is a vertical section of the above apparatus.
Figure 3:
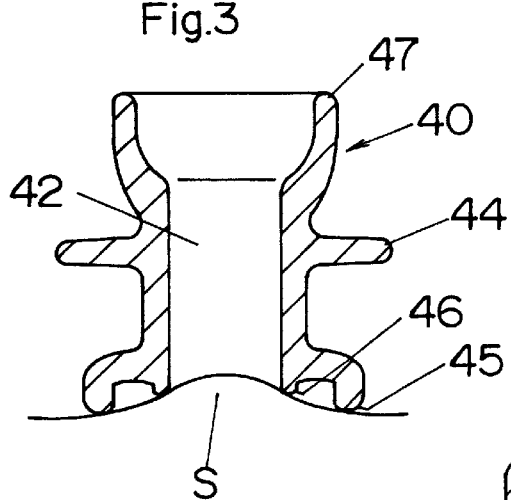
FIG. 3 is a diagram of illustrating the operation of the above apparatus.

First Embodiment <FIGS. 1 to 3>

Referring now to FIG. 1, there is shown a facial aesthetic treatment apparatus in accordance with a first embodiment of the present invention. The apparatus is composed of a elongated housing 10 shaped to be gripped by a hand of a user, and an attachment 40 adapted in use to apply a vacuum to a facial skin for removing a dirt, sebum or the like debris from the skin. The housing 10 is of an elongated configuration having a longitudinal axis and incorporates therein a diaphragm pump 20, a motor 14 driving the pump, and a battery 16 energizing the motor which are aligned along the longitudinal axis of the housing. Formed at the upper end of the housing 10 is a head 11 with a recess 12 through which a nozzle 30 extends for detachably carrying the attachment 40 at its upper end. The nozzle 30 is secured at its lower base to the housing 10 and has a through-hole 31 extending along the longitudinal axis of the housing. A cap 1 is provided on the top end of the housing to cover the attachment 40 and the nozzle 30.

The pump 20, which is secured to the lower end of the nozzle 30, includes a pump casing 21 and a reciprocator 22 connected by means of diaphragms 23 to the pump casing to define therebetween a pump chamber 24. The reciprocator 22 is connected through an eccentric cam 25 to an output shaft 15 of the motor 14 so as to draw an outside air into the pump chamber through an intake port 26 with a check valve (not shown) and force it out through an exhaust port 28 with a check valve (not shown) as the reciprocator is driven by the motor to reciprocate. The intake port 26 communicate with the through-hole 31 of the nozzle 30 to apply the suction force through the attachment 40 to a facial skin for the facial treatment, as shown in FIG. 3.

The attachment 40 is formed to have annular edges of different configurations at opposite ends of an axial bore 42, one with double annular edges and the other with a single annular edge. Each of the opposite ends of the attachment can be adapted to be pressed into contact with the facial skin for facial treatment.

Operation of the apparatus will be now discussed with the double annular edges 45 and 46 in contact with the facial skin. In order to avoid the skin from being subject to the suction force over a long period which would cause pain or bruise in the skin being treated, it is preferred to tap the attachment repeatedly to the skin in such a manner as to place the annular edges in contact with the skin intermittently. Further, the tapping is preferred to be made in such a manner that the annular edge are disengaged from the skin firstly at one peripheral portion of the edges and subsequently at the other portion thereof. This is achieved simply by twisting the wrist of the user holding the housing 10 when lifting off the attachment 40 from the skin. As shown in FIG. 3, while the annular edges 45 and 46 are kept in contact with the skin, the skin portion S confined by the edges is drawn by vacuum into the attachment 40 to form a bulging portion of which foot is held against the inner edge. Thus, the skin portion S sees an abrupt displacement at the two separate areas, one at the vicinity of the outer annular edge 45 and the other at the vicinity of the inner edge 46. It is at these areas where the sebum or the like debris is most likely to be squeeze out of the skin pores. The debris pulled away from the skin by vacuum will adhere to the interior wall of the attachment adjacent the annular edges. The front end of the nozzle 30 is covered with a filter 32 for preventing the debris from proceeding into the pump 20.

The opposite single annular edge 47 of a relatively small opening can be used without being tapped on the skin and is rather used in such a manner as to skid the edge along the skin over the nosewing. Because of the elliptical configuration given to the annular edge 47, the attachment 40 can be skid easier in the direction along its minor axis than along the major axis. That is, in moving the attachment in the direction along the minor axis, the bulging skin portion will exert less resistance than along the major axis. As a consequence of skidding the annular edge 47 along the skin, the debris squeezed out of the skin pore can be successfully scraped and collected on the edge of the attachment. Thus, the annular edge 47 of elliptical configuration is particularly advantageous for facilitating the skidding movement, yet giving a large treatment area for effective removal of the debris. The attachment 40 is mounted and demounted to and from the nozzle by holding a ring 44 projecting outwardly from the lengthwise center of the attachment 40.

As shown in FIG. 2, a bypass section path 50 extends from the root of the nozzle 30 in a radial direction and terminates at an open-air end 51, in parallel with a main suction path extending through the nozzle and the attachment towards the skin of the user. The main portion of the bypass suction path 50 is defined by an insert 53 secured to the housing 10. The open-air end 51 is exposed on the exterior of the housing to be readily accessible by a finger, i.e., the thumb of the user's hand gripping the housing 10, and is formed as a round hole of which diameter is greater towards the exterior of the housing 10 to be capable of being closed by the finger of the user's hand. Further, the open-air end 51 is surrounded by a raised rim 52 so that the user can easily locate the open-air end by feeling for the rim.

In use, when making the facial treatment, the user is required to close the open-air end 51 by the finger so as to apply the suction force through the nozzle 30 and the attachment 40. When the user feels a pain or any discomfort during the facial treatment, the suction force can be immediately released from applying to the skin simply by removing the finger from the open-air end 51 to communicate the nozzle with the open air. As a consequence, the skin portion having been pulled into the attachment can be immediately made free from the suction force and therefore be easily disengaged from the attachment 40 for assuring safe and easy removal of the attachment from the skin. Thus, the simple closing and opening of the open-air end 51 can activate and deactivate the suction force acting on the facial skin such that the facial treatment can be made over a wide area of the skin portion by intermittently applying the suction force, but without resorting to frequently turning on and off the pump. Further, the suction force can be adjusted to an optimum by pressing the finger to the open-air end 1 at a varying degree, i.e., varying an amount of the negative pressure escaping through the open-air end.

Figure 4:
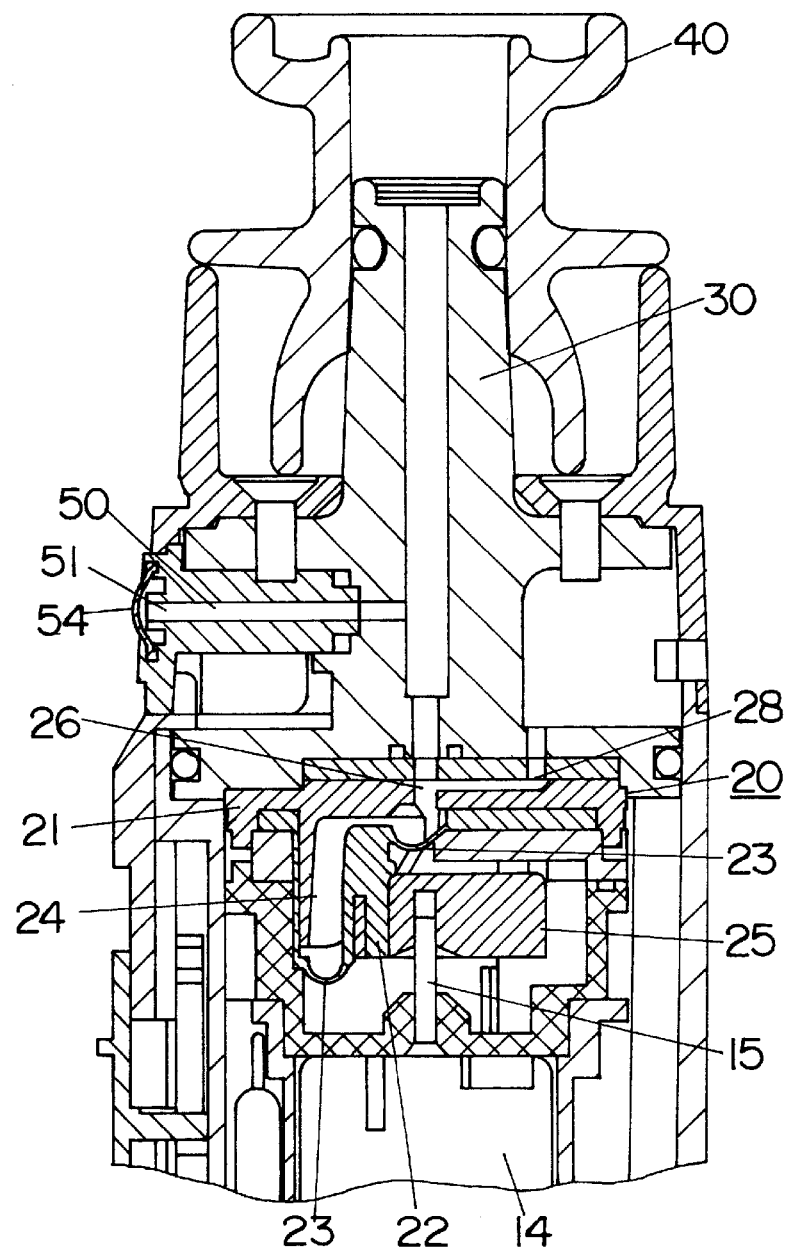
FIG. 4 is a vertical section of a major portion of a facial aesthetic treatment apparatus in accordance with a modification of the first embodiment.

FIG. 4 shows a modified apparatus which is identical to the first embodiment except for a provision of a flexible cover 54 for the open-air end 51. The flexible cover 54, which is exposed on the exterior of the housing to be accessible by the finger of the user, is normally held at a position of leaving the open-air end 51 opened and is resiliently deformed as a result of being pressed by the finger into a close position of closing the open-air end 51. In the normal open position, the open-air end 51 is kept in communication with a large volume of an interior of the housing 10 for escaping the negative pressure being developed by the pump. With the addition of the flexible cover 54, the open-air end 51 can be prevented from being clogged by foreign matters for assuring reliable safe operation of the apparatus. Other structures of the apparatus are identical to the first embodiment and therefore like parts are designated by like numerals as in the first embodiment.

Second Embodiment <FIGS. 5A and 5B>

FIGS. 5A and 5B show a facial aesthetic treatment apparatus in accordance with a second embodiment of the present invention which is identical to the first embodiment except that a switch handle 18A is configured to have a shutter section 19 at its upper end for selectively opening and closing an open-air end 51A of a like bypass suction path 50A. Like parts are designated by like numerals with a suffix letter of "A". The switch handle 18A is slidable between an OFF-position (FIG. 5A) of deenerging the motor 14A to stop the pump 20A and an ON-position (FIG. 5B) of energizing the motor 14A to operate the pump 20A. The shutter section 19 formed as an integral part of the switch handle 18A closes the open-air end 51A as the switch handle 18A comes into the ON-position, and opens the open-air end 51A as the switch handle 18A comes into the OFF-position. Thus, the negative pressure being applied to the skin portion through the attachment can be released as soon as the switch handle 18A is manipulated into the OFF-position, thereby allowing the attachment 40A to be easily removed from the skin.

Third Embodiment <FIGS. 6A and 6B>

FIGS. 6A and 6B show a facial aesthetic treatment apparatus in accordance with a third embodiment of the present invention which is identical to the first embodiment except that a nozzle 30B is floatingly supported to the housing 10B to define a contractible bypass suction path 50B between the nozzle and a base 34 supporting the nozzle. Like parts are designated by like numerals with a suffix letter of "B". The base 34 is secured to the housing 10B to extend over the pump 20B and is coupled to the nozzle 30B by means of a resilient bellows 35 such that the nozzle 30B is axially movable between a retracted position of FIG. 6B and an extended position of FIG. 6A. In the absence of an external force, the nozzle 30 is retained at the extended position by resiliency given to the bellows 35 where the lower end of the nozzle 30A is spaced from the base 34 to define therebetween the contractible bypass suction path 50B communicating the through-hole 31A of the nozzle 30A with an outside air. When making the facial treatment, the nozzle 30A is forced into the retracted position as a consequence of that the attachment 40B is pressed against the skin S, as shown in FIG. 6B, where the lower end of the nozzle 30B abuts against the base 34 to close the bypass suction path, thereby applying the suction force only to the skin for removal of the debris. As soon as the user wants to stop the facial treatment, the user is only required to pull the housing 10B away from the skin S, causing the nozzle 30B to assume the extended position, as shown in FIG. 6A. Whereby, the bypass suction path 50B is reestablished to release the negative pressure having been acting on the skin, allowing the easy removal of the attachment 40B from the skin. It could be also possible to adjust the suction force being applied to the skin by varying a distance between the nozzle 30B and the base 34, i.e., flow resistance of the bypass suction path 50B. This is accomplished by adjusting a degree of pushing the housing towards the skin. In order to keep the nozzle 30B in an axial alignment with the housing 10B, the base 34 is provided with guide projections 36 in slidable engagement with corresponding grooves 37 in the lower end of the nozzle 30B. The base 34 is formed with an aperture 38 for communication between the intake port 26B of the pump 20B and the through hole 31B of the nozzle 30B.

Fourth Embodiment <FIGS. 7 to 12>

Referring to FIGS. 7 and 8, there is shown a facial aesthetic treatment apparatus in accordance with a fourth embodiment of the present invention which is similar to the first embodiment and uses the same attachment 40C. Like parts are designated by like numerals with a suffix letter of "C". The apparatus comprises an elongated housing 10C which is configured to be gripped by one hand of a user and incorporates a diaphragm pump 20C, a motor 14C, and a battery 16C. Formed at the top end of the housing 10C is a recess 12C from the bottom of which a nozzle 30C projects for detachable connection to the attachment 40C. The nozzle 30C is of a tubular configuration having a through-hole 31C and is secured to the housing 10C immediately adjacent to the pump 20C.

The diaphragm pump 20C has a pump casing 21C and a diaphragm 23C which define therebetween the pump chamber 24C. The diaphragm 23C carries an external reciprocator 22C which is connected through an eccentric cam 25C to an output shaft 15C of the motor 14C so that the rotational motion of the output shaft is translated into a reciprocatory motion of the diaphragm 23C, thereby drawing an outside air through an intake port 26C with a check valve 27 and forcing it out through an exhaust port 28C with a check valve 29. The intake port 26C is in communication with the through-hole 31C of the nozzle 30C for applying the resulting suction force to a facial skin through the attachment 40C. A switch handle 18C on the exterior of the housing 10C is interlocked with an electric switch 17C connecting the battery 16C and the motor 14C for turning on and off the motor.

Figure 9:
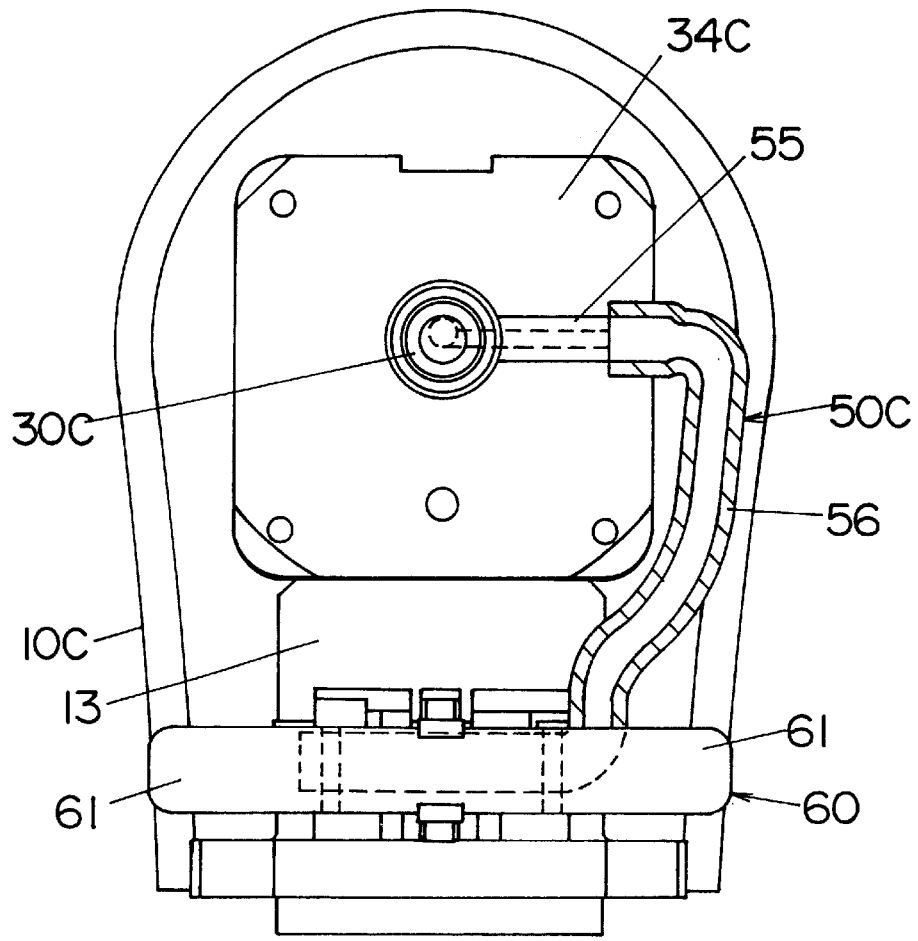
FIG. 9 illustrates an internal structure of a head portion of the above apparatus.
Figure 10:
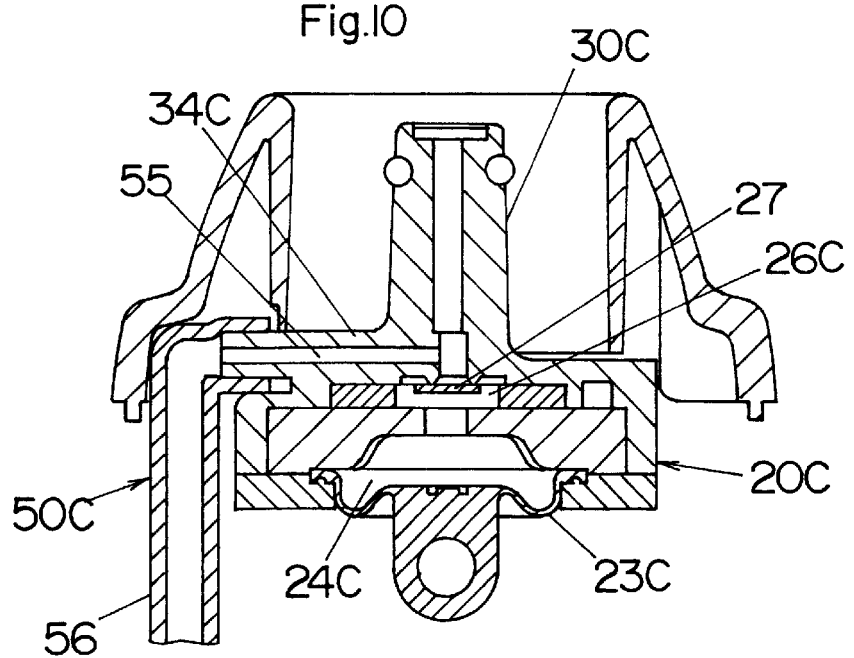
FIG. 10 is a sectional view of the head portion.
Figure 11A:
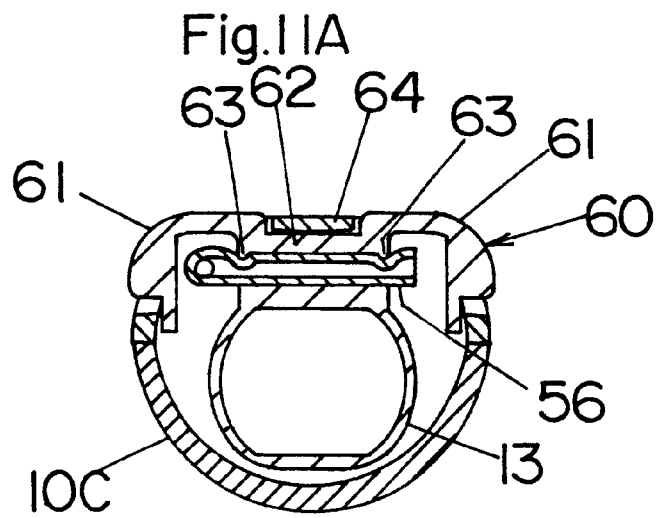
FIGS. 11A to 11C are diagrams illustrating an operation of regulating a suction force being applied to a user's skin.
Figure 11B:
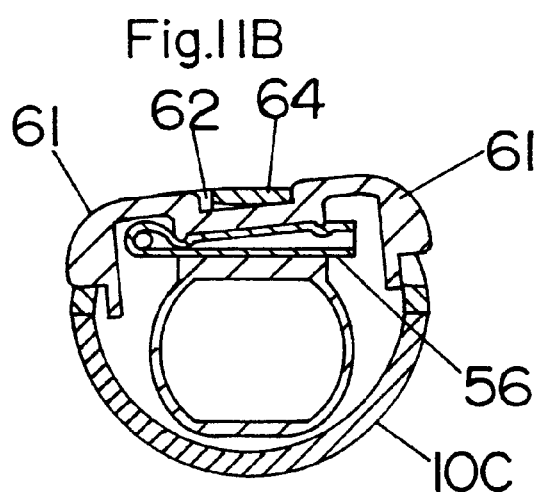
Figure 11C:
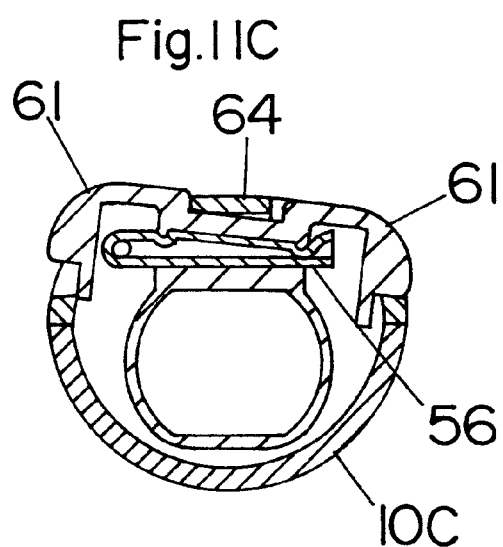

As shown in FIGS. 9 to 11, a bypass suction path 50C extends from the root of the nozzle 30C to an open-air end 51C in parallel with a main suction path extending through the nozzle 30C and the attachment 40C. The bypass suction path 50C is defined partly by a radial channel 55 extending through the base 34C of the nozzle 30C and partly by a resilient tube 56 extending from the channel 55 and having the open-air end 51C. The tube 56 extends from one lateral side of the base 34C of the nozzle 30C and is routed downward to a point above the switch handle 18C where it is bent to extend horizontally in contact with a motor casing 13 to be supported thereon by a suitable fitting. An actuator bar 60 is disposed on the side of the housing 10C in an opposed relation to the horizontal section of the tube 56. As best shown in FIG. 7 and FIGS. 11A to 11C, the actuator bar 60 has two button sections 61 respectively at its opposite ends, a center recess 62 between the button sections 61, and a pair of laterally spaced bumps 63 on the rear surface of the actuator bar. The actuator bar 60 is swingably supported to the housing 10C with the center recess 62 engaged with a fulcrum section 64 of the housing 10C so that it is swingable about the fulcrum section 64 with the bumps 63 being kept in pressed contact with the tube 56.

Figure 12C:
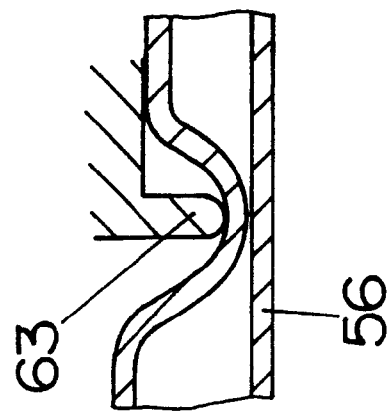
FIGS. 12A to 12C are diagrams illustrating an operation of variably regulating the suction force.
Figure 12B:
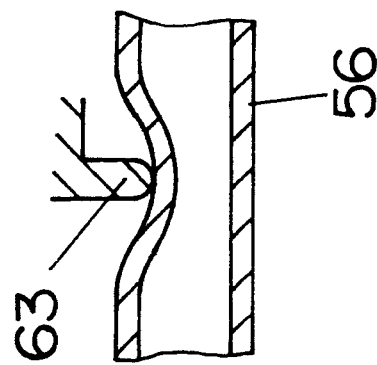
Figure 12A:
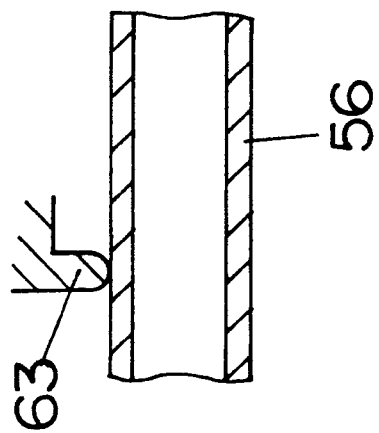

FIG. 11A shows a neutral position where the actuator bar 60 is kept straight by resiliency of the tube, giving no substantial force of deforming or squeezing the tube 56 to keep it opened. This is a condition where the negative pressure or the suction force developed by the pump is released through the bypass suction path so as to apply no substantial suction force to the facial skin through the attachment. When either of the button sections 61 is pressed, the actuator bar 60 is caused to swing against the resiliency of the tube 56 towards a position of FIG. 11B or FIG. 11C where one of the bumps 63 squeezes the corresponding portion of the tube to a full extent, thereby closing the tube or the bypass suction path 50C. Thus, the suction force given by the pump is fully applied through the attachment to the skin for the facial treatment. It is noted in this connection that, as shown in FIGS. 12A to 12C, an escaping rate of the negative pressure through the open-air end of the tube can be regulated by varying a pressing force applied to the button section, i.e., to the tube through the bump 63. Therefore, during the facial treatment, it is easy to adjust the suction force being applied to the skin for optimum performance. Anyway, the regulation and removal of the suction force being applied to the skin can be made simply by pressing or releasing the button sections with the one finger of the user's hand gripping the housing. Further, as best shown in FIG. 7, the button sections 61 is disposed on opposite sides of the housing 10C with respect to the longitudinal axis of the housing so that either of left-handed or right-handed users can be easy to access one of the button sections for regulation of the suction force.

Fifth Embodiment <FIGS. 13 to 19>

Figure 13:
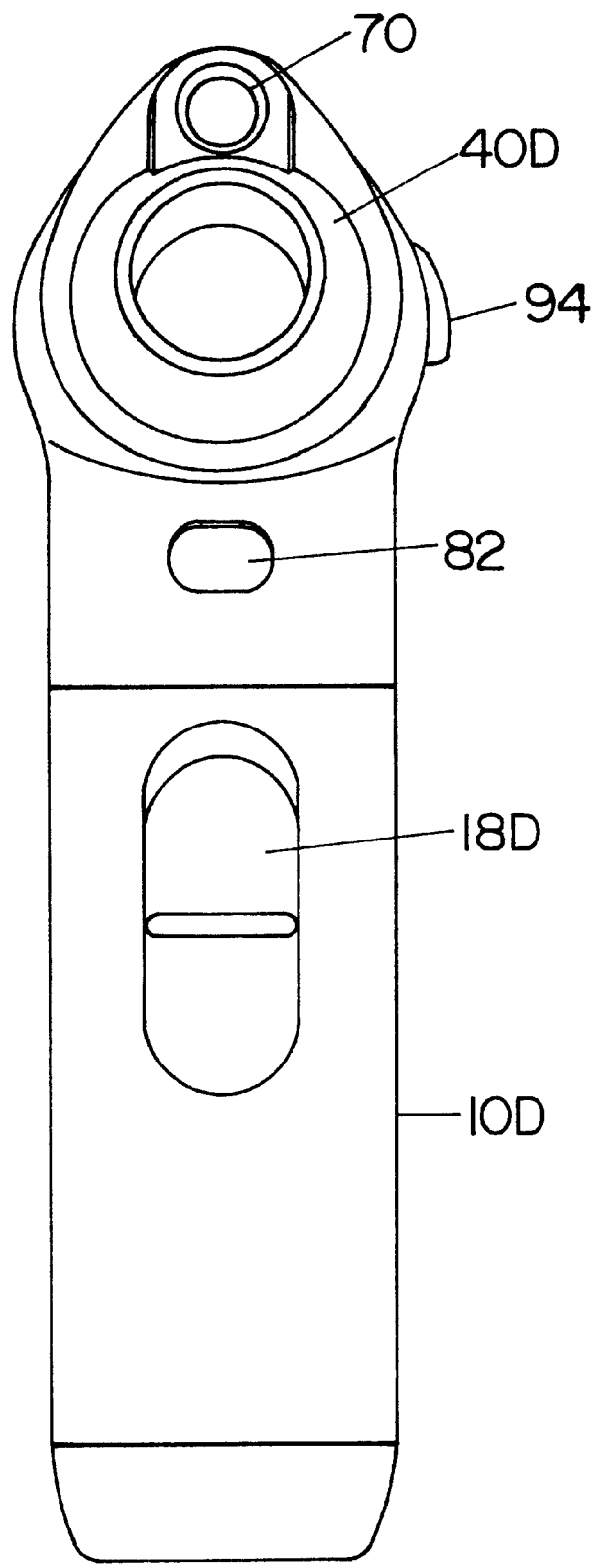
FIG. 13 is a front view of a facial aesthetic treatment apparatus in accordance with a fifth embodiment of the present invention.
Figure 14:
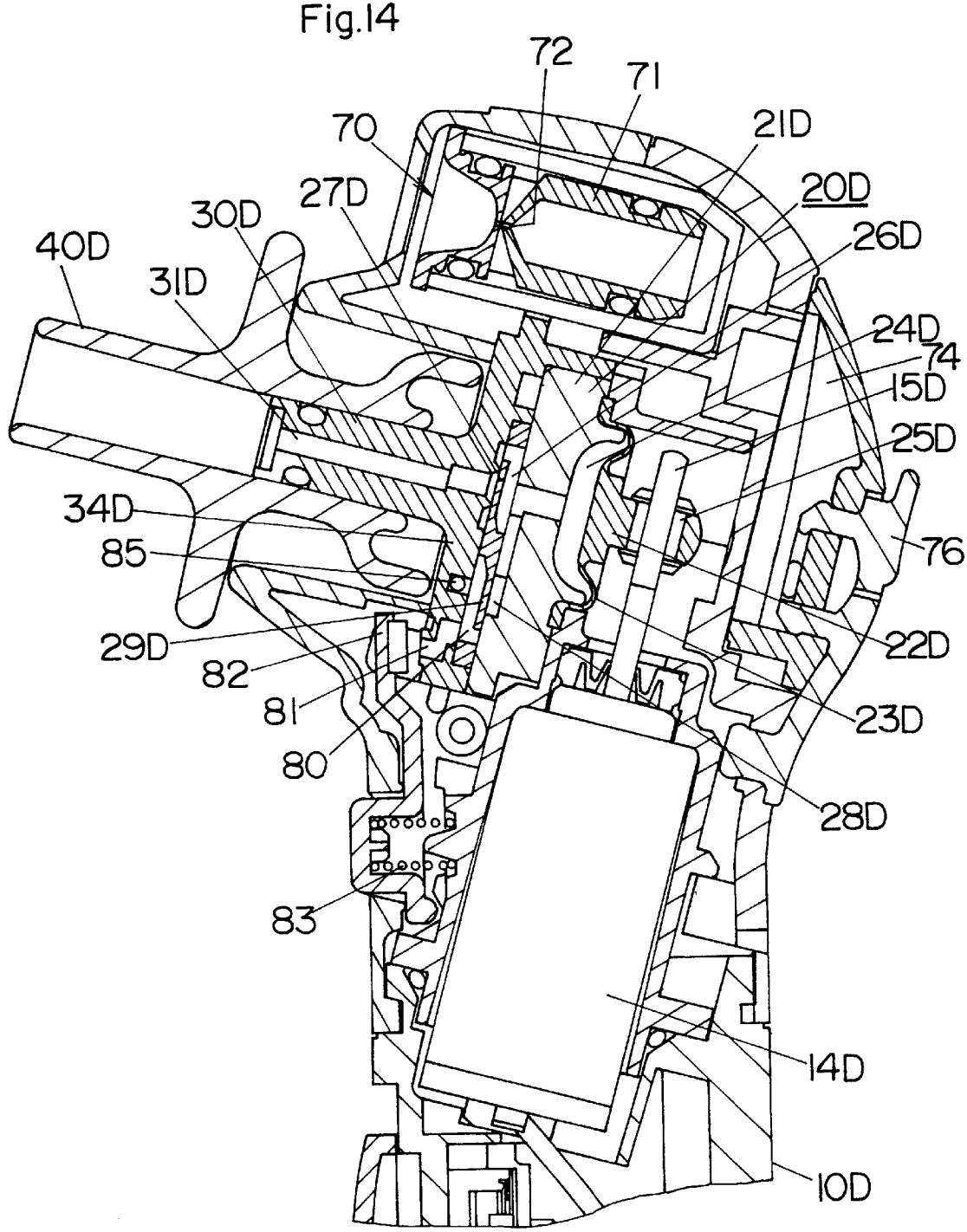
FIG. 14 is a vertical section of a major portion of the above apparatus.
Figure 15:
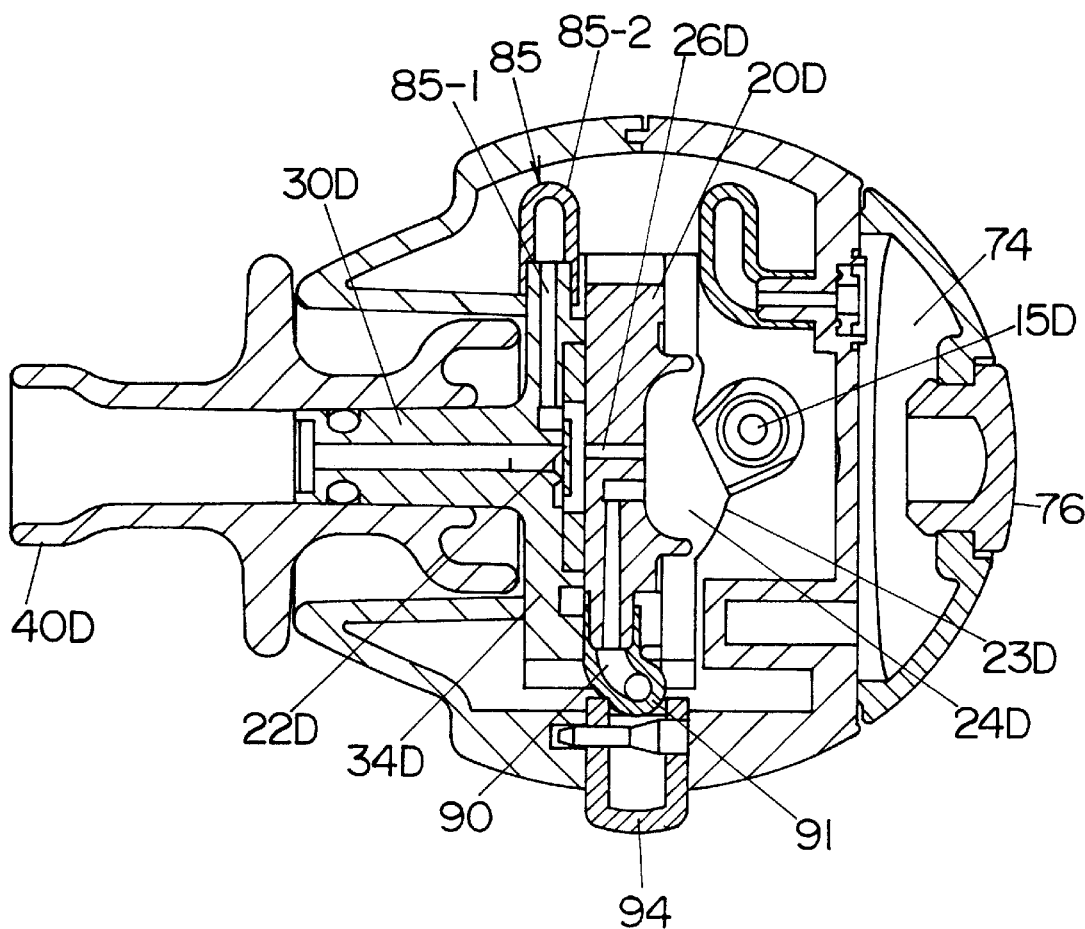
FIG. 15 is a horizontal section of the major portion of the above apparatus.

Referring to FIGS. 13 and 14, a facial aesthetic treatment apparatus in accordance with a fifth embodiment of the present invention is shown to additionally include a humidifier 70 provides a stream of mist to the user's face during the facial treatment with the use of the suction force or independently thereof. The other structure and operation are similar to those of the third embodiment. Therefore, like parts are designated by like numerals with a suffix letter of "D".

The humidifier 70 is activated by making the use of an exhaust air from a like diaphragm pump 20D utilized to give the suction force for facial treatment with an attachment 40D. Firstly, the structure of the pump with added function of supplying the exhaust air to the humidifier is discussed. The pump 20D comprises a pump casing 21D and a diaphragm 23D which defines therebetween a pump chamber 24D. The diaphragm 23D carries a reciprocator 22D which is connected through an eccentric cam 25D to an output shaft 15D of the motor 14D so that the rotational motion of the output shaft is translated into a reciprocatory motion of the diaphragm 23C, thereby drawing an outside air through an intake port 26D with a check valve 27D and forcing it out through an exhaust port 28D with a check valve 29D. The pump casing 21D is secured to the housing 10D together with a base 34D of the suction nozzle 30D. The suction nozzle 30D is formed as an integral part of the base 34D and have the through-hole 31D in communication with the intake port 26D of the pump.

Figure 18A:
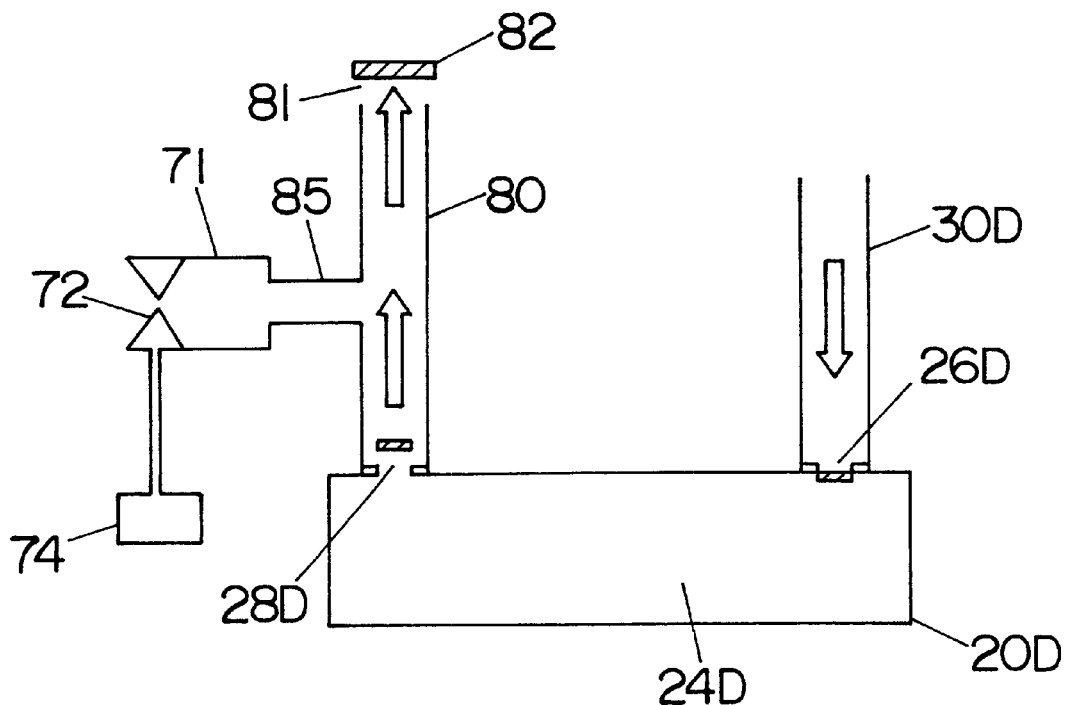
FIG. 18A and 18B are schematic diagrams illustrating a mist generating operation of the above apparatus.
Figure 18B:
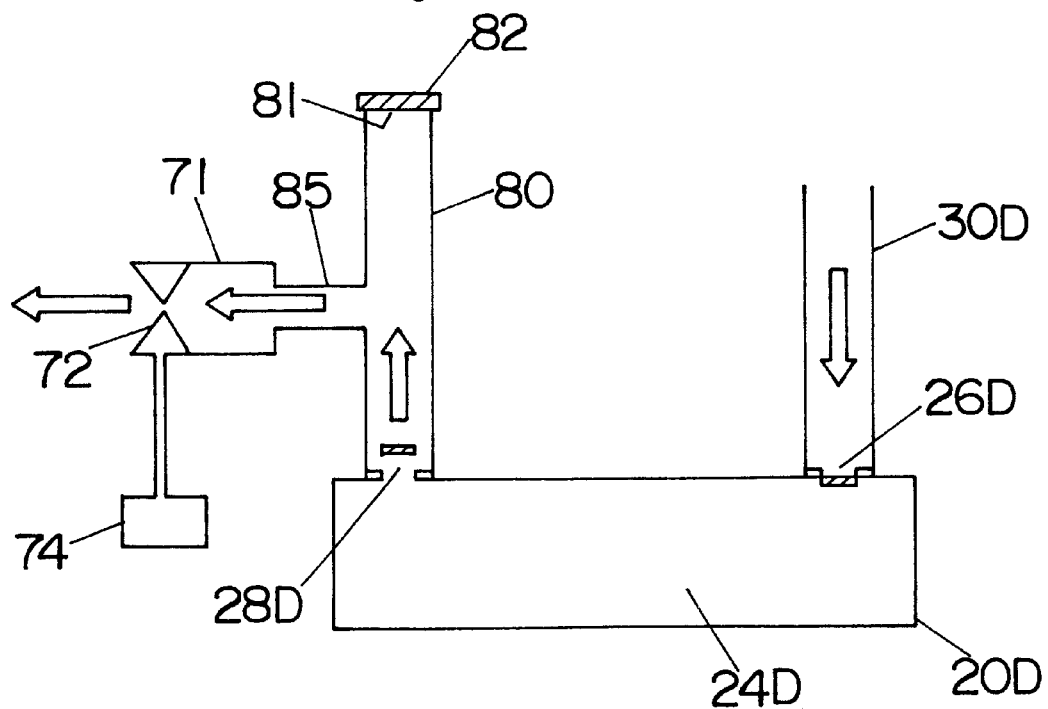

Formed between the pump casing 21D and the base 34D is an exhaust path 80 extending from the exhaust port 28D to an exit port 81 which opens to the outside air and is selectively closed by a push-button switch 82. The switch 82 is disposed above the switch handle 18D and is biased by a spring 83 into a normal position of opening the exit port 81. In the normal operation of the pump for applying the suction force to the facial skin, the exit port 81 is opened so that the exhaust air is discharged from the pump chamber through the exhaust port 28D, the exhaust path 80 and the exit port 81, as shown in FIG. 18A. A bypass exhaust path 85 diverges from the exhaust path 80 at a portion between exit port 81 and the exhaust port 28D in order to feed the exhaust air, i.e., a pressurized air to the humidifier, when the exit port 81 is closed by the switch 82, as shown in FIG. 18B, for generation of the stream of the mist.

The humidifier 70 comprises a spray nozzle 71 disposed above the suction nozzle 30D in a parallel relation thereto, a water tank 74 supplied with a volume of water through a rear supply port with a lid 76. The spray nozzle 71 has a constriction 72 which is connected to the water tank 74 through a water hose 84 to be fed with water therefrom. As shown in FIGS. 14 to 17, the bypass exhaust path 85 is defined partly by a channel 85-1 formed in the base 34D of the nozzle and partly by a flexible hose 85-2 extending from the base 34D to the rear end of the spray nozzle 71 so as to feed the exhaust air to the spray nozzle in response to the closure of the exit port 81 by the switch 82. The exhaust air thus introduced into the spray nozzle 71 generates an air jet flowing through the constriction 72 where the water is sucked up into the air jet to give the stream of mist directed out through a front end of the spray nozzle 71. Thus, the user can be easy to enjoy the stream of mist either alone or in combination with the facial treatment due to the sucking force.

Figure 16:
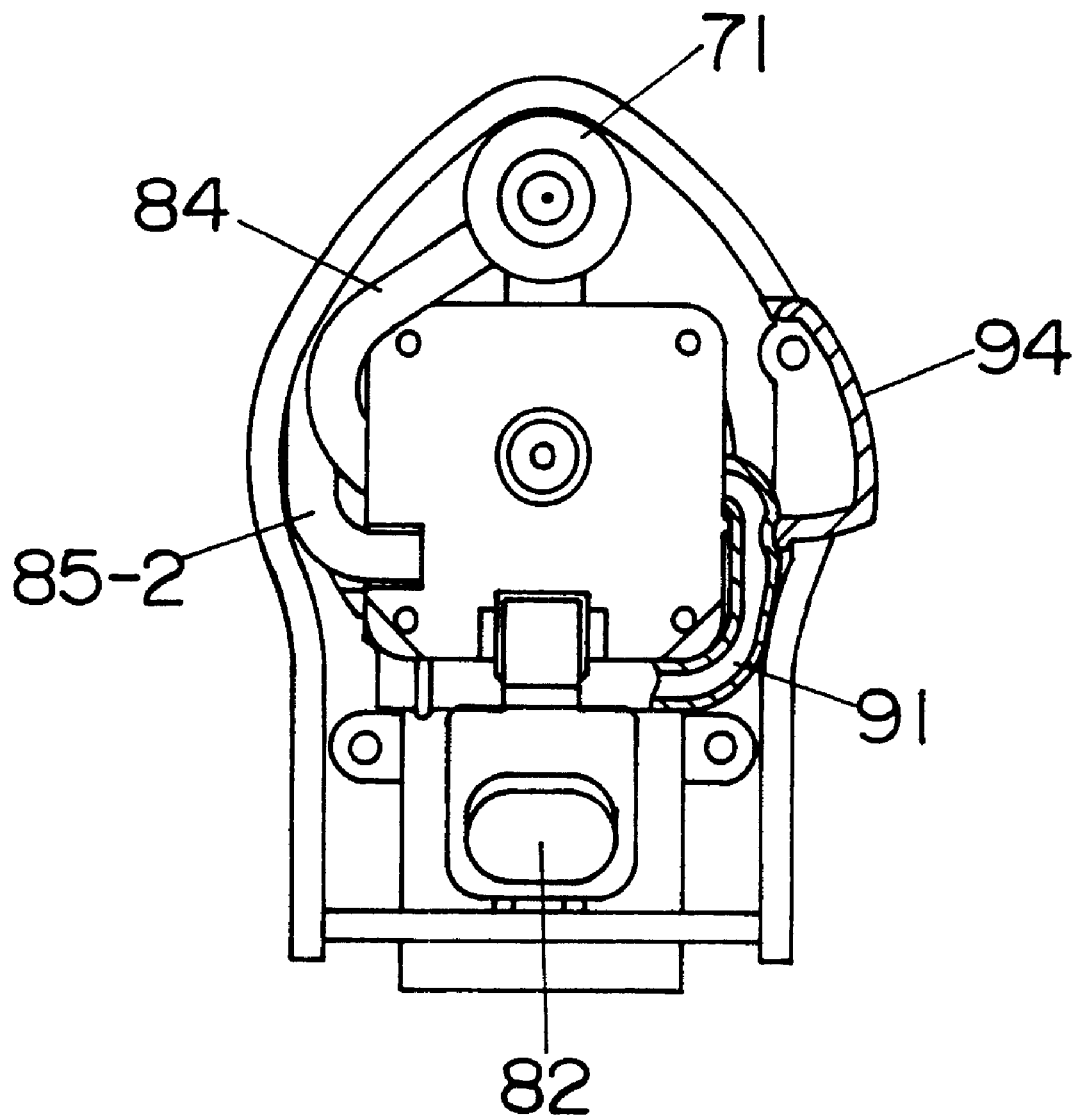
FIG. 16 is a front view illustrating an internal structure of a head portion of the above apparatus
Figure 17:
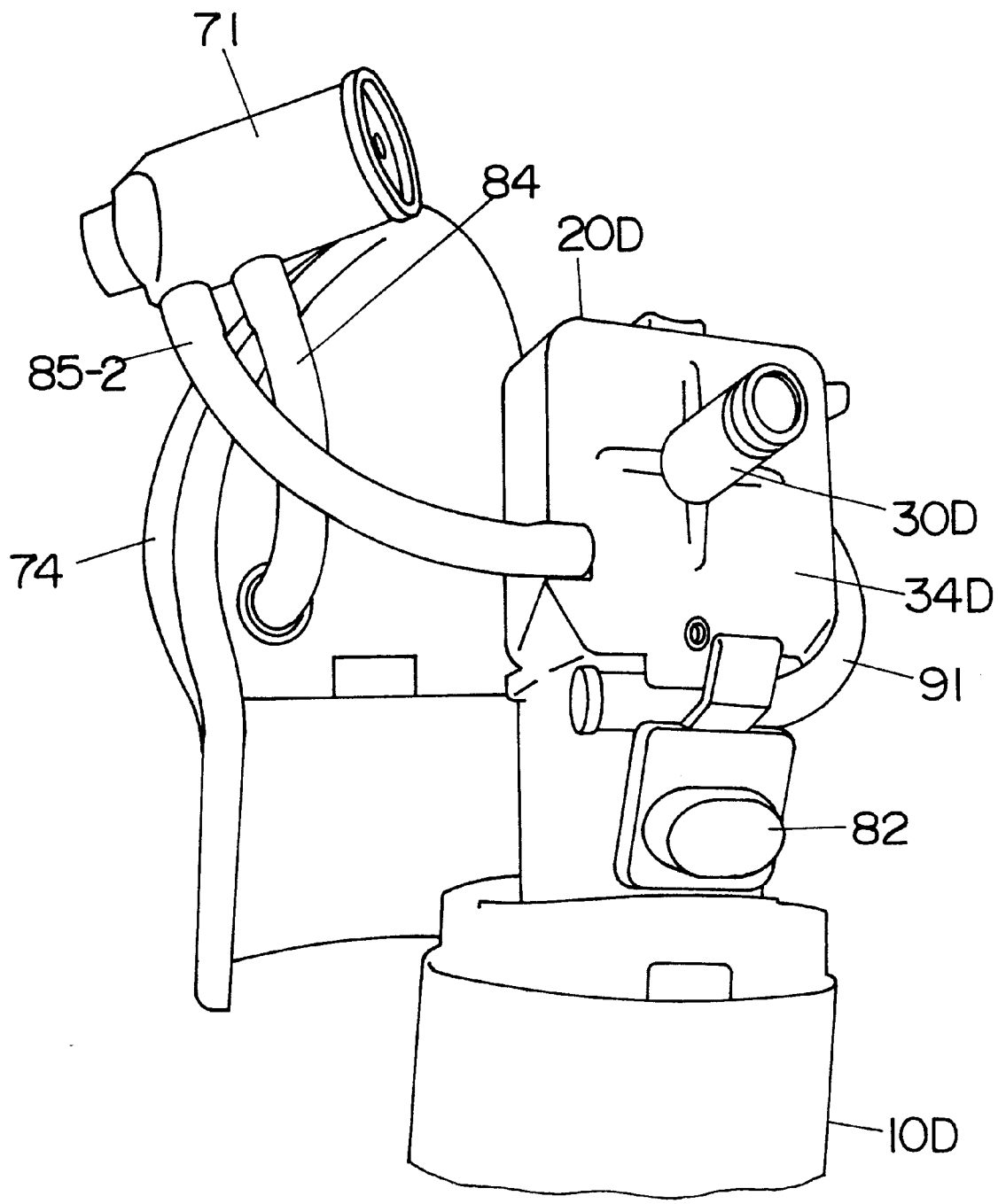
FIG. 17 is a perspective view of the major portion of the above apparatus.

In this embodiment, the sucking force being applied to the skin can be adjusted by use of a regulator which is somewhat different from that of the previous embodiments. As best shown in FIGS. 19A and 19B, the regulator comprises an auxiliary chamber 90 in communication of the pump chamber 24D and an actuator 94 for varying a volume of the auxiliary chamber. The auxiliary chamber 90 is defined by a resilient tube resilient tube 91 which extends from the lateral side of the pump casing 21D to a portion immediately below the pump casing 21D, as best shown in FIGS. 16 and 17. The actuator 94 is in the form of a lever switch of which one end is pivotally connected to the housing 10D to have the other end held in engagement with a portion of the resilient tube 91, as shown in FIG. 16. The actuator 94 is disposed on one side of a head portion of the housing well within a reach of the finger of the user's hand gripping the housing. In the absence of an external force, the actuator 94 is kept at a normal position where it gives no substantial force of deforming or squeezing the tube. As the actuator 94 is pressed to an increasing extent, the tube 91 is deformed to correspondingly reduce the volume of the additional chamber 90, i.e., the total volume of the pump chamber effective for the pumping action, thereby regulating the suction force being developed by the pump and applied to the skin. Thus, optimum and safe facial treatment can be assured.

What is claimed is:

1. A facial aesthetic treatment apparatus comprising:
   a housing provided with a nozzle and a suction pump for developing a suction force through said nozzle;
   a tubular attachment adapted to be coupled to said nozzle for applying the suction force to facial skin for removing sebum or like debris from the facial skin; and
   a regulator which alters pump characteristics of said suction pump to regulate the suction force being applied through said nozzle to the facial skin, wherein said regulator comprises a resilient tube extending from said nozzle to an open-air end to define a bypass suction path, and an actuator being held in a contactable relation with a portion of said resilient tube for pressing said actuator against said resilient tube to close said bypass suction path to a varying extent.

2. The apparatus as set forth in claim 1, wherein said housing is of an elongated configuration having a longitudinal axis and said actuator comprises a pair of button sections exposed on an exterior of said housing to be accessible by a finger of a user's hand gripping the housing, said pair of button sections arranged on opposite sides of said housing about said longitudinal axis.

\* \* \* \* \*